United States Patent [19]

Peters et al.

[11] 4,397,949
[45] Aug. 9, 1983

[54] PREPARATION AND IMMOBILIZATION OF INULINASE

[75] Inventors: Peter J. H. Peters; Pieter L. Kerkhoofs, both of Geleen, Netherlands

[73] Assignee: Stamicarbon, B.V., Geleen, Netherlands

[21] Appl. No.: 278,612

[22] Filed: Jun. 29, 1981

[30] Foreign Application Priority Data

Jun. 27, 1980 [NL] Netherlands ......................... 8003723

[51] Int. Cl.$^3$ ...................... C12P 19/14; C12N 11/10; C12N 11/08; C12N 9/24
[52] U.S. Cl. ...................................... 435/99; 435/174; 435/178; 435/180; 435/182; 435/200
[58] Field of Search ................. 435/99, 200, 174, 178, 435/180, 181, 182, 814, 201, 195

[56] References Cited

U.S. PATENT DOCUMENTS

| | | | |
|---|---|---|---|
| 4,170,696 | 10/1979 | Hirohara et al. | 435/180 X |
| 4,239,854 | 12/1980 | Hirohara et al. | 435/180 X |
| 4,277,563 | 7/1981 | Kerkhoffs | 435/99 |
| 4,334,027 | 6/1982 | Klein et al. | 435/182 X |

FOREIGN PATENT DOCUMENTS 26672 4/1981 European Pat. Off. .
53-8608578 7/1978 Japan .

OTHER PUBLICATIONS

Kierstan et al., The Immobilization of Microbial Cells, Subcellular Organelles and Enzymes in Calcium Gels, Biotech. & Bioemg., vol. XIX, 1977, (pp. 387-397).
Dobrolinskayz et al., Biosynthesis of Beta-Fructofuranosidase by Fungi of the Genus Aspergillus, Chem. Abst., vol. 82:41845r, 1975, (p. 317).
Iyenger et al., Innulinase. Chem. Abstr., vol. 30:8254-8257, 1936.
Nakamura et al., Studies on Microbial Inulase. Chem. Abstr., vol. 90:99073u, 1979, (p. 183).
Nakamura et al., Studies on Microbial Inulase. Chem. Abstr., vol. 88:1324452, 1978, (p. 177).

Primary Examiner—David M. Naff

[57] ABSTRACT

Enzyme preparations are obtained from *Aspergillus phoenicis* having high inulinase activity, a very low Michaelis constant, thermal stability, optimum inulinase activity across a wide pH range, and little sensitivity to heavy metal ion inhibition. The enzyme may be immobilized on an organic macroporous polymer or in an alginate gel.

16 Claims, No Drawings

PREPARATION AND IMMOBILIZATION OF INULINASE

BACKGROUND AND SUMMARY OF THE INVENTION

The present invention relates to the preparation and application of enzyme preparations having inulinase activity.

It is already known that fructose polymers (inulins) can be hydrolyzed with enzymes to fructose. The enzyme can be obtained from cultures of, among others, *Saccharomyces fragilis, Candida kefyr, Asperqillus niger* and *Fusarium roseum*. To carry out the hydrolysis on an industrial scale, an enzyme preparation having maximum activity, a great stability and an optimum effect in a weakly acid medium is desirable.

The present invention provides an enzyme preparation having these desirable characteristics.

DETAILED DESCRIPTION

According to the present invention an enzyme preparation having inulinase activity is obtained from a culture of *Aspergillus phoenicis*. An enzyme preparation having a high inulinase activity, a very low Michaelis constant, and showing an optimum inulinase activity in a favorable pH range can be obtained from such a culture. The thermal stability of the enzyme preparation is advantageously high. The enzyme shows only slight inhibition by heavy-metal ions and no substrate inhibition. As a further advantage, the enzyme having inulinase activity is present extracellularly in cultures of *Aspergillus phoenicis*.

Particularly suitable for the preparation of an enzyme preparation having inulinase activity is the strain *Aspergillus phoenices* CSB 294.80, filed by applicant with the Centraal Bureau voor Schimmelculturen at Baarn, the Netherlands. *Aspergillus phoenicis* is described in "The Genus Aspergillus" by K. B. Raper and D. I. Fennel (Baltimore 1965), pages 307–309 the disclosure of which is incorporated herein by reference. Mutants or variants of *Aspergillus phoenicis* can also be employed.

The mold can be pre-cultured on already known substrates. Suitable substrates include for example, solid substrates such as those consisting of agar in a solution of malt-extract, bactopeptone, inulin and salts. The spores are harvested and transferred into a stirred culture vessel suitable for aerobic culture growth.

A medium can be employed which consists of an aqueous buffered solution containing a biologically assimilable nitrogen, carbon and phosphorous source. If desired, spore elements can be added. For instance, a suitable medium consists of a sterilized solution of 20 grams yeast extract, 1 gram of sodium ammonium phosphate, 0.5 gram of ammonium sulphate and 15 grams of inulin in one liter of water. Adding glucose is not desired since glucose is converted into acids. The formation of the desired enzyme is accelerated due to the small amount of inulin present in the medium.

The pH of the medium must be kept at a value of at least 4.0. Little or no inulinase-active enzyme is formed at a lower pH. The pH is preferably kept at a value of between about 5 and about 7. A particularly suitable pH range is between about 5.5 and about 6.0.

The temperature of the culture may be between about 20° C. and about 40° C. Most preferably a temperature between about 25° C. to about 30° C. is employed.

Culturing is carried out under aerobic conditions. About 85% of the total quantity of the inulinase-active enzyme formed is present extracellularly.

After a culture time of about 4 to about 10 days the liquid phase will contain a sufficient quantity of the desired enzyme. For example, after 8 days of culturing at 28° C. and at a pH between 5.5 and 6.0 a culture medium having a 36 I.U./ml activity was obtained. One I.U. is defined as the production of 1 micromole of product per minute under assay conditions. After removing the cells, an enzyme solution is obtained which can then be even further concentrated, if desired, by distilling off water at reduced pressure. The enzyme can be obtained in solid form, for example, by employing freeze drying, spray drying or solution drying by evaporation.

This enzyme product can be classified as inulinase (or inulase) EC 3.2.1.7.

The free enzyme obtained according to the present invention is a distinct improvement over already known enzymes having inulinase activity. The enzyme of the present invention has a maximum activity at about 60° C. or somewhat higher while at a pH of between about 3.5 to about 4.5. The Michaelis constant $K_m$ is about $2 \times 10^{-6}$ M/l. This is considerably lower than the Michaelis constant values for other already known enzymes having inulinase activity. Therefore, the enzyme obtained according to the present invention can more easily and more fully hydrolyze inulin than the other already known enzymes having inulinase activity.

The enzyme of the present invention also shows little sensitivity to known heavy metal ion inhibitors, such as Hg(II). The literature describes already known enzymes having inulinase activity obtained from cultures *Aspergillus niger* as being very sensitive to inhibition by Hg(II).

Furthermore, the enzyme of the present invention has a very low invertase activity, whereas enzymes obtained from yeast cultures generally have rather high invertase activity.

The enzyme of the present invention can be used in the free, water-soluble form. For industrial uses the enzyme is preferably employed in a water-insoluble, immobilized form. The immobilization can be effected by employing usual methods. For instance, the enzyme can be disposed in a polymer matrix such as a polyacrylamide gel, an alginate gel such as calcium or sodium alginate gel or cellulose acetate. In addition, an immobilized inulinase-active enzyme preparation can be obtained by forming a reaction suspension of an inulinase-active enzyme solution and a resin, which resin is obtained by reacting an organic macroporous polymer containing reactive groups such as amino and/or hydroxyl groups with glutardialdehyde to absorb the enzyme on the resin. The immobilized inulinase-active enzyme is recovered therefrom. The enzyme can also be adsorbed on an ion exchanger, although this form of immobilization is reversible and is, therefore, not preferred. Furthermore, it is, possible to cross-link the enzyme, in the presence of a filler if desired, with a bifunctional reagent, such as a dicarboxylic acid or anhydride thereof, a dialdehyde or a diisocyanate. The enzyme solution can also be reacted with a reactive group-containing macroporous polymer such as, polyacrylicacid anhydride, a styrene-maleic anhydride copolymer or a poly-(methylvinylether)-maleic anhydride copolymer. The enzyme can also be reacted with a synthetic or natural solid having reactive groups. Suitable solids include, for example, glass, steel, silica, alumina, an ion exchanger resin, pumice, sponge, activated carbon or mineral. These and other methods have generally been described in detail in the literature and will be well understood by those skilled in the art.

Preferably, the immobilized enzyme should retain a low Michaelis constant and have an optimum activity over a wide pH range of from about 4.0 to about 5.5 or somewhat higher. Consequently pH fluctuations during the hydrolysis are permissible. This makes it easier to employ the immobilized enzyme.

The enzyme can be used in free form for the hydrolysis of inulin recovered from vegetable material. The extraction from the vegetable material can also be combined with the hydrolysis as described in published Dutch patent application No. 7,811,389, corresponding to U.S. application Ser. No. 95,680 filed Nov. 19, 1979, now U.S. Pat. No. 4,277,563, the disclosure of which is incorporated herein by reference. By preference, the enzyme is used in an immobilized form for the hydrolysis of an inulin-containing solution. The immobilized enzyme can also be used in a fixed bed, a fluidized bed or in a stirred tank reactor.

Preferably, inulin hydrolysis is carried out at a pH of between about 4.0 and about 6.0, at a temperature of between about 20° C. and about 65° C. and at an inulin concentration of between about 5% and about 30% by weight of the substrate solution. In this regard inulin means all oligomers and polymers occurring in nature, consisting of one unit derived from glucose and 2 or more units derived from fructose. Inulin can be obtained from, among other things, dahlia tubers, the roots of Jerusalem artichoke and chicory.

EXAMPLE I

The strain of *Aspergillus phoenicis* CBS 294.80 as inoculated on the following, presterilized, fixed medium: 30 grams of malt extract, 5 grams of bactopepton (Oxoid Ltd.), 0.5 grams of ammonium sulphate, 5 grams of inulin (product code 2327 of J. T. Baker Chemicals, Deventer, Holland), 0.2 grams of KCl, 20 grams of agar, 1 liter water. After culturing for 7 days at 28° C., the spores that formed were harvested.

A culture medium was prepared by sterilizing a solution of 20 grams yeast extract, 1 gram sodium ammonium phosphate, 0.5 grams ammonium sulphate and 15 grams inulin in 1 liter of water. The pH of this culture medium was 5.5. The previously harvested spores were introduced into the medium. Culturing was then carried out for 7 days while stirring (200 rpm) at 28° C. Subsequently, the cells were removed by centrifugation. The remaining liquid containing the inulinase active enzyme which had formed had an activity of 36 I.U./ml. The liquid was evaporated to dryness at 40° C. under reduced pressure. The solid obtained was subsequently dissolved again in water to the original volume. The activity of the liquid thus obtained was equal to the original activity. Therefore, the thermal stability of the enzyme was good.

The activity of the free enzyme depended on the pH, with an optimum level at pH 3.5, and also on the temperature, with an optimum level at just over 60° C. The Michaelis constant, $K_m$, of the free enzyme was 10 mg/ml. The inulin used had a molecular weight of about 5000 which corresponded to a $K_m$ of about $2 \times 10^{-6}$ M/l.

Adding $HgCl_2$ until the $HgCl_2$ was present in an amount of 0.5% by weight of solution had hardly any effect on the enzymatic activity.

EXAMPLE II 25 liters of an 0.5 M calcium chloride solution containing 0.5% by weight of inulin and 0.13% by weight of a surface active agent (Tween-80) was introduced into a 15 cm diameter and 200 cm long column. As described in Example I a homogeneous mixture was prepared using a 750 ml cell-free culture medium from a culture of *Aspergillus phoenicis* CBS 294.80, and 1750 ml 2% (wt) sodium-alginate solution. The mixture was slowly fed, by drops, into the top of the column with a precision metering device. In this process pellets having equal dimensions formed and sank to the bottom of the column. After the whole mixture had been fed into the column, the pellets were filtered off and then, while stirring, were washed successively with an 0.5 M calcium chloride solution, water and an 0.1 M acetate buffer (pH 5.0).

The resultant immobilized enzyme preparation was used for the hydrolysis of inulin. 10 kg of a 10% (wt) inulin solution was brought to a pH of 5.0 using phosphate and was stirred for 1 hour at 50° C. with the above obtained quantity of immobilized enzyme. High pressure liquid chromatography showed that the inulin was fully hydrolyzed. The sugar solution that formed was separated off by filtration. 97% by weight of the sugars formed consisted of fructose.

EXAMPLE III

A macroporous phenol-formaldehyde resin having hydroxyl groups (Duolite S761 of Dia-Prosim, France) was thoroughly and successively washed with ethanol, water, diluted lye, diluted hydrochloric acid, diluted lye and 0.15 M phosphate buffer. Subsequently, 25 ml of the resin was stirred for one hour at room temperature with a mixture of 25 ml 0.15 M phosphate buffer (pH 7.7) and 6 ml 25% by weight glutar-dialdehyde solution. The final pH was 6.5. The modified resin was then filtered off and subsequently added to a mixture, cooled to 4° C., of 1.05 grams of the enzyme solution obtained as described in Example I and 24 ml 0.15 M phosphate buffer. After stirring the suspension for 20 hours at 4° C., the solid was filtered off and washed with a 1.5 M phosphate buffer at a pH of 6.5. By comparing the activity of the free enzyme solution with the activity of the immobilized enzyme preparation obtained in the manner described above it was found that the immobilization activity efficiency was 41.8%.

Testing showed that the immobilized enzyme preparation obtained had an optimum degree of activity and was virtually stable in the pH range between 4.5 and 6.0. The activity depended on the temperature. An optimum temperature is at or just over 60° C. The $K_m$ was 20 mg/l which corresponds to $4 \times 10^{-6}$ M/l for the conversion of inulin having a molecular weight of abut 5000.

Similar immobilized enzyme preparations can be obtained by starting from other resins, such as, Duolite A-7 (a phenol-formaldehyde resin containing amino groups.

What is claimed is:

1. An inulinase-active enzyme preparation having insensitivity to heavy metal ion inhibition obtained by:
    (a) culturing an *Aspergillus phoenicis* mold culture for a period of several days under aerobic conditions in an aqueous medium containing a biologically assimilable nitrogen, carbon and phosphorus source and including inulin, at a pH of at least 4.0 up to about 7.0 and at a temperature of about 20° C. to about 40° C., and (b) recovering the inulinase-active enzyme solution thereby produced.

2. An enzyme preparation according to claim 1 wherein said culture medium is free of glucose.

3. An enzyme preparation according to claim 1 or 2 wherein said mold culture is *Aspergillus phoenicis* CBS 294.80.

4. An inulinase-active enzyme preparation according to claim 1 or 2 wherein said inulinase-active enzyme is classified as inulinase or inulase EC 3.2.1.7.

5. An immobilized water-insoluble inulinase-active enzyme preparation having insensitivity to heavy metal ion inhibition obtained by:

(a) culturing an *Aspergillus phoenicis* mold culture for a period of several days under aerobic conditions in an aqueous medium containing a biologically assimilable nitrogen, carbon and phosphorus source and including inulin at a pH of at least 4.0 up to about 7.0 and at a temperature of about 20° C. to about 40° C.;

(b) thereafter recovering the inulinase-active enzyme solution which is thereby formed;

(c) forming a reaction suspension of a resin in said enzyme solution, wherein said resin is obtained by reacting an organic macroporous polymer containing amino groups, hydroxyl groups or combinations thereof with glutardialdehyde, to adsorb said enzyme on said resin and thereby obtain an immobilized enzyme; and (d) thereafter recovering said immobilized enzyme from said suspension.

6. An immobilized inulinase-active enzyme composition having insensitivity to heavy metal ion inhibition prepared by:

(a) culturing an *Aspergillus phoenicis* mold culture for a period of several days under aerobic conditions in an aqueous medium containing a biologically assimilable nitrogen, carbon and phosphorus source and including inulin at a pH of at least 4.0 up to about 7.0 and at a temperature of about 20° C. to about 40° C.;

(b) thereafter recovering the inulinase-active enzyme solution which is thereby formed;

(c) admixing said enzyme solution with an alginate solution and gelling the alginate to produce an alginate gel containing the enzyme immobilized therein; and (d) thereafter recovering said immobilized enzyme composition which is thereby formed.

7. An enzyme composition according to claim 6, wherein said alginate solution is a calcium or sodium alginate solution.

8. A process for obtaining an inulinase-active enzyme preparation having insensitivity to heavy metal ion inhibition by culturing a microorganism and recovering the inulinaseenzyme consisting essentially in the combination of steps of:

(a) culturing an *Aspergillus phoenicis* mold culture for a period of several days under aerobic conditions in an aqueous medium containing a biologically assimilable nitrogen, carbon and phosphorus source and including inulin at a pH of at least 4.0 up to about 7.0 and at a temperature of about 20° C. to about 40° C.; and (b) thereafter recovering the inulinase-active enzyme solution which is thereby formed.

9. Process according to claim 8, wherein in step (a) said pH is between about 5 and about 7.

10. Process according to claim 8 or 9, wherein in step (a) said temperature between about 25° C. and 30° C.

11. Process according to claim 8 wherein said recovery step (b) further includes concentrating said solution of inulinase-active enzyme by removing water.

12. Process according to claim 8, wherein in step (a), said pH is between 5.5 and 6.0.

13. Process according to claim 8, wherein said culture period is between 4 and 10 days.

14. A process for obtaining an immobilized water-insoluble inulinase-activity enzyme composition having insensitivity to heavy metal ion inhibition, consisting essentially in the combination of steps of:

(a) culturing an *Aspergillus phoenicis* mold culture for a period of several days under aerobic conditions in an aqueous medium containing a bioligically assimilable nitrogen, carbon and phosphorus source and including inulin at a pH of at least 4.0 up to about 7.0 and at a temperature of about 20° C. to about 40° C.;

(b) thereafter recovering the inulinase-active enzyme solution which is thereby formed;

(c) forming a reaction suspension of a resin in said enzyme solution, wherein said resin is obtained by reacting an organic macroporous polymer containing amino groups, hydroxyl groups or combinations thereof with glutardialdehyde, to adsorb said enzyme on said resin and thereby obtain an immobilized enzyme; and (d) thereafter recovering said immobilized enzyme from said suspension.

15. In a process for hydrolyzing inulin with an immobilized inulinase-active enzyme preparation having insensitivity to heavy metal ion inhibition, the improvement consisting essentially in the combination of steps of:

(a) culturing an *Aspergillus phoenicis* mold culture for a period of several days under aerobic conditions in an aqueous medium containing a biologically assimable nitrogen, carbon and phosphorus source and including inulin at a pH of at least 4.0 up to about 7.0 and at a temperature of about 20° C. to about 40° C.; and (b) recovering the inulinase-active enzyme solution which is thereby formed;

(c) forming an immobilized water-insoluble inulinase-active enzyme preparation from said enzyme solution;

(d) preparing an inulin containing solution; and (e) hydrolyzing the inulin in said inulin-containing solution with said immobilized enzyme preparation at a pH between 4 and 6 and at a temperature between 20° C. and 65° C. and at an inulin concentration in said inulin-containing solution of between about 5% to about 30% by weight based on the substrate solution.

16. In a process for hydrolyzing inulin according to claim 15, wherein said immobilization is effected by forming a reaction suspension of a resin in said enzyme solution, wherein said resin is obtained by reacting an organic macroporous polymer containing amino groups, hydroxyl groups or combinations thereof with glutardialdehyde, to adsorb said enzyme on said resin and thereby obtain an immobilized enzyme.

* * * * *